(12) United States Patent
Nguyen et al.

(10) Patent No.: US 7,699,897 B2
(45) Date of Patent: Apr. 20, 2010

(54) METHOD OF COLORING HAIR

(75) Inventors: Nghi Van Nguyen, Edison, NJ (US); David W. Cannell, Plainfield, NJ (US); Sawa Hashimoto, Westfield, NJ (US); Cynthia Espino, Princeton, NJ (US)

(73) Assignee: L'Oreal, Paris (FR)

( * ) Notice: Subject to any disclaimer, the term of this patent is extended or adjusted under 35 U.S.C. 154(b) by 109 days.

(21) Appl. No.: 11/855,861

(22) Filed: Sep. 14, 2007

(65) Prior Publication Data

US 2009/0070945 A1    Mar. 19, 2009

(51) Int. Cl.
*A61Q 5/10* (2006.01)

(52) U.S. Cl. .................... 8/405; 8/406; 8/409; 8/410; 8/435; 8/550; 8/551; 8/582; 132/202; 132/208

(58) Field of Classification Search ............ 8/405, 8/406, 409, 410, 435, 550, 551, 582; 132/202, 132/208
See application file for complete search history.

(56) References Cited

U.S. PATENT DOCUMENTS

| | | | |
|---|---|---|---|
| 3,689,424 A | 9/1972 | Berg et al. | |
| 3,883,356 A | 5/1975 | Syrovatka et al. | |
| 4,488,564 A | 12/1984 | Grollier et al. | |
| 5,196,188 A | 3/1993 | Potthoff-Karl et al. | |
| 5,360,581 A | 11/1994 | Rizvi et al. | |
| 5,891,956 A | 4/1999 | Smith et al. | |
| 5,897,870 A | 4/1999 | Schehlmann et al. | |
| 5,951,718 A | 9/1999 | Krutak et al. | |
| 6,139,853 A | 10/2000 | Akram et al. | |
| 6,410,005 B1 | 6/2002 | Galleguillos et al. | |
| 6,540,791 B1 * | 4/2003 | Dias ............... | 8/111 |
| 6,548,051 B2 | 4/2003 | Garnier et al. | |
| 6,589,517 B1 | 7/2003 | McKelvey et al. | |
| 6,740,130 B2 | 5/2004 | Sander et al. | |
| 7,083,655 B2 | 8/2006 | Pratt et al. | |
| 7,094,262 B2 | 8/2006 | Lagrange et al. | |
| 7,122,062 B2 | 10/2006 | Yamashita et al. | |
| 7,141,079 B2 | 11/2006 | Audousset et al. | |
| 2002/0034489 A1 | 3/2002 | Wiegland et al. | |
| 2006/0024255 A1 | 2/2006 | Quadir et al. | |

FOREIGN PATENT DOCUMENTS

WO    97/45510 A1    12/1997
WO    01/22928 A1    4/2001

* cited by examiner

*Primary Examiner*—Eisa B Elhilo
(74) *Attorney, Agent, or Firm*—Connoly Bove Lodge & Hutz LLP

(57) ABSTRACT

The disclosure relates to compositions and methods of using the compositions to color hair. The composition contains at least one polyamine, at least one acid, at least one water-insoluble ingredient, at least one hair colorant, solvent and optionally at least one auxiliary ingredient. The methods for coloring involve contacting hair with the composition of the disclosure.

27 Claims, No Drawings

METHOD OF COLORING HAIR

TECHNICAL FIELD

The disclosure relates to compositions and methods for coloring hair. The compositions and methods provide a water resistant and non-transferable protective barrier on keratinous substrates imparting the substrates with improved properties.

BACKGROUND OF THE DISCLOSURE

The disclosure relates to compositions and methods for coloring hair. Typically, hair is colored by application of dyes and/or bleaching agents (coloring agents). For optimum efficiency during the dyeing and/or the bleaching process, the coloring agents should be concentrated as much as possible on the hair fiber. In addition, a barrier to aid in highlighting and lowlighting hair would be useful. Such a barrier would allow coloring agents to selectively color portions of hair while leaving other portions of hair protected and uncolored thus giving highlights or lowlights in selected portions of the hair. Accordingly, a hair coloring composition that aids in the distribution of coloring agents onto the hair fiber would be useful in making more efficient use of hair coloring agents.

BRIEF SUMMARY OF THE DISCLOSURE

The disclosure relates to compositions and methods for coloring hair. The composition provides for a more efficient use of coloring agents by concentrating the color agents more directly onto the hair. The composition contains at least one polyamine (a), at least one acid (b), at least one water-insoluble ingredient (c), at least one hair colorant (d), solvent (e), and optionally at least one auxiliary ingredient (f). The method for coloring hair involves contacting the hair with the composition of the disclosure. The at least one colorant and at least one auxiliary ingredient components may be applied to hair before, during or after the application of components (a), (b) and (c) which may be applied to hair together.

DETAILED DESCRIPTION OF THE DISCLOSURE

The term "comprising" (and its grammatical variations) as used herein is used in the inclusive sense of "having" or "including" and not in the exclusive sense of "consisting only of". The terms "a" and "the" as used herein are understood to encompass the plural as well as the singular.

Other than in the operating examples, or where otherwise indicated, all numbers expressing quantities of ingredients and/or reaction conditions are to be understood as being modified in all instances by the term "about".

The term coloring hair means changing the color or shade of hair by use of dyes, pigments or bleaches or by use a combination of dyes, pigments and bleaches. The term coloring agent means a composition that colors hair. The coloring agent is typically a dye, a pigment or a bleach which may be used individually or in combination.

The term "water-insoluble" means those compounds which are either completely or partially insoluble in water.

"At least one" as used herein means one or more and thus includes individual components as well as mixtures/combinations.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The at least one polyamine (a) of the disclosure comprises at least two amino groups and typically comprises at least five amino groups and more typically comprises at least ten amino groups.

The at least one acid (b) comprises at least one acid group. The at least one acid (b) may also comprise 2 or more acid groups (a polyacid).

Amino groups include primary amino groups, secondary amino groups and tertiary amino groups and further includes amino groups which are terminal, pendant and intercalated in a skeleton of the at least one polyamine compound.

In an embodiment of the disclosure the composition for coloring hair comprises:
(a) at least one polyamine,
(b) at least one acid,
(c) at least one water-insoluble ingredient,
(d) at least one hair colorant
(e) solvent and
(f) optionally at least one auxiliary ingredient wherein the ratio of the amine number of the at least one polyamine to the acid number of the at least one acid is from about 1:0.5 to about 1:30 and wherein a mixture of components (a), (b), (c), and (e) form a mixture that has a contact angle of at least about 66 degrees on glass. Typically, the ratio of the amine number to the acid number is from about 1:0.8 to about 1:20 and more typically from about 1:0.9 to about 1:15 and even more typically from about 1:1 to about 1:10.

Another embodiment of the disclosure involves coloring hair with the disclosed composition.

The order of application of components (a)-(e) and optional component (f) to the hair is not limited. Each applied component may be alone or with any other component or mixture of components in any order to the hair.

For example, the at least one coloring agent (d) may be applied to hair before the other components, with the other components or after the other components.

Embodiments may include first dying and/or bleaching with the coloring agent (d) then applying the other components of the disclosure (a), (b), (c), (e) and optionally (f) to the hair.

Other embodiments may include applying all the components of the disclosure as a single mixture.

Yet other embodiments may include applying components (a), (b), (c), (e) and optionally component (f) to the hair then coloring the hair with component (d).

The applications described above may be conducted selectively on the hair. That is, some portions of the hair may be first colored with the coloring agent followed by application of the other components and other portions may have all components except the coloring agent (d) applied followed by application of the coloring agent. Again the method of applying the individual components and the order of addition of the components not limited.

The at least one polyamine (a) may, for example, be chosen from a polyethyleneimine, a polyvinylamine, an aminated polysaccharide, an amine substituted polyalkylene glycol, an amine substituted polyacrylate crosspolymer, an amine substituted polyacrylate, an amine substituted polymethacrylate, an aminosilicone, a protein, an amine substituted polyester, a polyamino acid, an amodimethicone, a polyalkylamine, diethylene triamine, triethylenetetramine, spermidine, spermine and mixtures thereof.

Non-limiting examples of polyethyleneimine include Lupasol® products commercially available from BASF. Suitable examples of Lupasol® polyethyleneimines include Lupasol® PS, Lupasol® PL, Lupasol® PR8515, Lupasol® G20, Lupasol® G35 as well as Lupasol® SC Polyethyleneimine Reaction Products (such as Lupasol® SC-61B, Lupasol® SC-62J, and Lupasol® SC-86X). Other non-limiting examples of polyethyleneimines which may be used in the composition according to the present invention are the Epomin® products commercially available from Aceto. Suitable examples of Epomin® polyethyleneimines include Epomin® SP-006, Epomin® SP-012, Epomin® SP-018, and Epomin® P-1000. These examples include substituted polyethyleneimines.

Non-limiting examples of polyvinylamines include Lupamines® 9095, 9030, 9010, 5095 and 1595 from BASF.

An example of an amine substituted polyalkylene glycol includes PEG-15 cocopolyamine from Cognis.

An example of an aminosilicone includes Dow Corning® 2-8566 Amino Fluid, an amino functional polydimethylsiloxane fluid from Dow Corning®.

In another embodiment, the at least one polyamine compound is chosen from proteins and protein derivatives. Non-limiting examples of suitable proteins and protein derivatives for use in the present invention include those listed at pages 1701 to 1703 of the C.T.F.A. International Cosmetic Ingredient Dictionary and Handbook, $8^{th}$ edition, vol. 2, (2000) (incorporated herein by reference). In one embodiment, the at least one polyamine compound is chosen from wheat protein, soy protein, oat protein, collagen, and keratin protein.

In another embodiment, the at least one polyamine compound is chosen from compounds comprising lysine, compounds comprising arginine, compounds comprising histidine, and compounds comprising hydroxylysine. Not limiting examples include chitosan, polyarginine and polylysine.

An example of an amine substituted polyacrylate crosspolymer includes Carbopol® Aqua CC polymer from Lubrizol Advanced Materials, Inc.

In the present disclosure, the at least one polyamine is used in a positive amount up to about 30% by weight, more typically a positive amount up to about 10% by weight, and most typically a positive amount up to about 5% by weight, based on the weight of the composition as a whole. In some embodiments the at least one polyamine ranges from about 0.1% to about 30% by weight based on the weight of the composition. In other embodiments the at least one polyamine ranges from about 0.1 wt % to about 10 wt %, based on the weight of the composition as a whole and in further embodiments the range is from about 0.1 wt % to about 5 wt %.

The at least one acid (b) of the composition may, for example, be chosen from a fatty carboxylic acid, a fatty ether carboxylic acid, a fatty ether phosphoric acid, a fatty phosphoric acid and mixtures thereof. The at least one acid (b) may contain one or 2 or more acid groups (a polyacid).

Non-limiting examples of fatty carboxylic acids includes fatty acids having from about 6 to about 40 carbon atoms corresponding formula (I)

RCOOH (I)

wherein:

R is a hydrocarbon radical containing from about 6 to about 40 carbon atoms. In addition, R is linear or branched, acyclic or cyclic, saturated or unsaturated, aliphatic or aromatic, substituted or unsubstituted. Typically, R is a linear or branched, acyclic $C_{6-40}$ alkyl or alkenyl group or a $C_{1-40}$ alkyl phenyl group, more typically a $C_{8-22}$ alkyl or alkenyl group or a $C_{4-18}$ alkyl phenyl group, and even more typically a $C_{12-18}$ alkyl group or alkenyl group or a $C_{6-16}$ alkyl phenyl group.

Suitable fatty acids having from about 6 to about 40 carbon atoms include, but are not limited to the following representatives referred to by their INCI names (INCI: nomenclature for raw materials according to the International Cosmetic Ingredient Dictionary, $10^{th}$ Edition, published by the Cosmetic, Toiletry and Fragrance Association Inc. (CTFA), Washington D.C., USA): Arachidic Acid, Arachidonic Acid, Beeswax Acid, Capric Acid, Caproic Acid, Caprylic Acid, Coconut Acid, Isostearic Acid, Lauric Acid, Linoleic Acid, Linolenic Acid, Myristic Acid, Oleic Acid, Olive Acid, Palmitic Acid, Rapeseed Acid, Stearic Acid, Behenic Aid, Tallow Acid, Undecanoic Acid, Undecylenic Acid, 18-Methyleicosanoic Acid, Wheat Germ Acid and mixtures thereof.

Typical fatty acids having from about 6 to about 40 carbon atoms include Linoleic Acid, Oleic Acid, Isostearic Acid, and Stearic Acid.

Non-limiting examples of fatty ether carboxylic acid includes compounds corresponding to formula (II):

$$RO[CH_2O]_u[(CH_2)_xCH(R')(CH_2)_y(CH_2)_zO]_v \\ [CH_2CH_2O]_wCH_2COOH \quad (II)$$

wherein:

R is a hydrocarbon radical containing from about 6 to about 40 carbon atoms;

u, v and w, independently of one another, represent numbers of from 0 to 60;

x, y and z, independently of one another, represent numbers of from 0 to 13;

R' represents hydrogen, alkyl, and the sum of x+y+z is $\geqq 0$;

Ether carboxylic acids corresponding to formula (II) can be obtained by alkoxylation of alcohols ROH with ethylene oxide as the sole alkoxide or with several alkoxides and subsequent oxidation. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formula (II), R is linear or branched, acyclic or cyclic, saturated or unsaturated, aliphatic or aromatic, substituted or unsubstituted. Typically, R is a linear or branched, acyclic $C_{6-40}$ alkyl or alkenyl group or a $C_{1-40}$ alkyl phenyl group, more typically a $C_{8-22}$ alkyl or alkenyl group or a $C_{4-8}$ alkyl phenyl group, and even more typically a $C_{12-18}$ alkyl group or alkenyl group or a $C_{6-16}$ alkyl phenyl group; u, v, w, independently of one another, is typically a number from 2 to 20, more typically a number from 3 to 17 and most typically a number from 5 to 15; x, y, z, independently of one another, is typically a number from 2 to 13, more typically a number from 1 to 10 and most typically a number from 0 to 8.

Suitable ether carboxylic acids or ether carboxylates include, but are not limited to, the following representatives referred to by their INCI names (INCI: nomenclature for raw materials according to the International Cosmetic Ingredient Dictionary, $7^{th}$ Edition, published by the Cosmetic, Toiletry and Fragrance Association Inc. (CTFA), Washington D.C., USA): Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, $C_{9-11}$ Pareth-6

Carboxylic Acid, $C_{11-15}$ Pareth-7 Carboxylic Acid, $C_{12-13}$ Pareth-5 Carboxylic Acid, $C_{12-13}$ Pareth-8 Carboxylic Acid, $C_{12-13}$ Pareth-12 Carboxylic Acid, $C_{12-15}$ Pareth-7 Carboxylic Acid, $C_{12-15}$ Pareth-8 Carboxylic Acid, $C_{14-15}$ Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid and mixtures thereof.

Typical Carboxylic Acids are Oleth-10 Carboxylic Acid, Laureth-5 Carboxylic Acid and Laureth-11 Carboxylic Acid.

Non-limiting examples of fatty phosphoric acids include compounds corresponding to Formula III:

$$R\text{—}O\text{—}P(O)(OH)_2 \qquad (III)$$

wherein:

R is a hydrocarbon radical containing from about 6 to about 40 carbon atoms. In addition, R is linear or branched, acyclic or cyclic, saturated or unsaturated, aliphatic or aromatic, substituted or unsubstituted. Typically, R is a linear or branched acyclic $C_{6-40}$ alkyl or alkenyl group or a $C_{1-40}$ alkyl phenyl group, more typically a $C_{8-22}$ alkyl or alkenyl group or a $C_{4-18}$ alkyl phenyl group and most typically a $C_{12-18}$ alkyl group or alkenyl group or a $C_{6-16}$ alkyl phenyl group.

Typical fatty phosphoric acids include capryl phosphate, caprylyl phosphate, lauryl phosphate, oleyl phosphate, isostearyl phosphate, stearyl phosphate and cetyl phosphate.

Non-limiting examples of fatty ether phosphoric acids compounds corresponding to formulas IV and V:

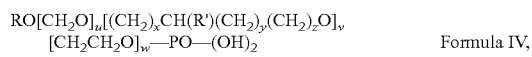

$$RO[CH_2O]_u[(CH_2)_xCH(R')(CH_2)_y(CH_2)_zO]_v$$
$$[CH_2CH_2O]_w\text{—}PO\text{—}(OH)_2 \qquad \text{Formula IV,}$$

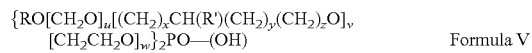

$$\{RO[CH_2O]_u[(CH_2)_xCH(R')(CH_2)_y(CH_2)_zO]_v$$
$$[CH_2CH_2O]_w\}_2PO\text{—}(OH) \qquad \text{Formula V}$$

and combinations thereof, wherein:

R is a hydrocarbon radical containing from about 6 to about 40 carbon atoms;

u, v and w, independently of one another, represent numbers of from 0 to 60;

x, y and z, independently of one another, represent numbers of from 0 to 13;

R' represents hydrogen, alkyl, and the sum of x+y+z being ≧0.

The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formulas IV and V, R is linear of branched, acyclic or cyclic, saturated or unsaturated, aliphatic or aromatic, substituted or unsubstituted, typically a linear or branched, acyclic $C_{6-40}$ alkyl or alkenyl group or a $C_{1-40}$ alkyl phenyl group, more typically a $C_{8-22}$ alkyl or alkenyl group or a $C_{4-18}$ alkyl phenyl group, even more typically a $C_{12-18}$ alkyl group or alkenyl group or a $C_{6-16}$ alkyl phenyl group; u, v, w, independently of one another, is typically a number from 2 to 20, more typically a number from 3 to 17 and most typically a number from 5 to 15; x, y, z, independently of one another, is typically a number from 2 to 13, more typically a number from 1 to 10 and most typically a number from 0 to 8.

Typical fatty ether phosphoric acids include PPG-5-Ceteth-10 phosphate (CRODAFOS SG), Oleth-3 phosphate (CRODAFOS N3 acid), Oleth-10 phosphate (CRODAFOS N10 acid), and a mixture of Ceteth-10 phosphate and Dicetyl phosphate (CRODAFOS CES) all sold by Croda.

Examples of the at least one acid (b) that contain 2 or more acid groups include Acrylates Copolymer, Acrylates/Octylacrylamide Copolymer, Acrylates/Octylacrylamide/Diphenyl Amodimethicone Copolymer, Octylacrylamide/acrylates/Butylaminoethyl Methacrylate Copolymer, Acrylates/Stearyl Acrylate/Ethylamine Oxide Methacrylate Copolymer, Acrylates/t-Butylacrylamide Copolymer, PEG/PPG-25/25 Dimethicone/Acrylates Copolymer, VA/Butyl Maleate/Isobornyl Acrylate Copolymer, PVM/MA Copolymer, Ethyl ester of PVM/MA Copolymer, Butyl Ester of PVM/MA Copolymer, VA/Crotonates Copolymer, VA/Crotonates/Vinyl Neodecanoate Copolymer, VA/Vinyl Butyl Benzoate/Crotonates Copolymer, Carbomer, Polystyrene sulfonic acid, Terephthalylidene Dicamphor Sulfonic Acid, Phenylbenzimidazole Sulfonic Acid, Polyacrylamidomethylpropane Sulfonic Acid, Dimethicone PEG-7 Phosphate, Dimethicone PEG-8 Phosphate, Dimethicone PEG-10 Phosphate, Dimethicone PEG/PPG-7/4 Phosphate, Dimethicone PEG/PPG-12/4 Phosphate, Lauryl dimethicone PEG-10 Phosphate, Polyperfluoroethoxymethoxy Difluoroethyl PEG Phosphate, Polyperfluoroethoxymethoxy PEG-2 Phosphate, Polyphosphorylcholine Glycol Acrylate, Cocoamphodipropionic Acid, Lauroamphodipropionic Acid, Lauriminodipropionic Acid, Polyacrylic Acid, Polymethacrylic Acid, Polyglutamic acid, Myristoyl Glutamic Acid, Lauroyl Glutamic Acid, Palmitoyl Glutamic Acid, Cocoyl Glutamic Acid.

The at least one acid (b) is present in the composition in a positive amount up to about 50% by weight, typically a positive amount up to about 30% by weight, and more typically a positive amount up to about 15% by weight, based on the weight of the composition as a whole. In other embodiments, the at least one acid (b) is present in the composition in a range of from about 2 to about 50% by weight and in a range from about 5 to about 15% by weight, based on the weight of the composition as a whole.

The at least one water-insoluble ingredient (c) may, for example, be chosen from an oil, a polymer, a fatty ester, a hydrocarbon, a silicone, a wax, a fatty acid (in addition to the fatty acid (b)), salts of fatty acids, a fatty alcohol and mixtures thereof.

Non-limiting examples of oils include plant oil such as olive oil, avocado oil, coconut oil, aloe vera oil, almond oil, castor oil, jojoba oil, peanut oil, sesame oil, hazelnut oil, sunflower oil, colza oil, grapeseed oil, linseed oil and palm oil.

Non-limiting examples of hydrocarbon oils include mineral oil, petrolatum, paraffins, iso-paraffins, aromatic hydrocarbons and $C_{10-40}$ hydrocarbons which may be aliphatic, aromatic, arylaliphatic or mixtures thereof and the aliphatic hydrocarbons may be straight chain, branched, cyclic or combinations thereof.

Non-limiting examples of silicones include phenyltrimethicone, dimethicone, cyclomethicone, dimethicone copolyol, aminosilicone, laurylmethicone copolyol, cetyl dimethicone, cetyl triethylammonium dimethicone copolyol phthalate, dimethicone copolyol lactate, silicone quaternium-13, stearalkonium dimethicone copolyol phthalate, stearaminopropyl dimethicone and polyorganosiloxanes such as polydimethylsiloxane.

Non-limiting examples of waxes include paraffin wax, beeswax, candelilla wax, carnauba wax, jasmine wax, jojoba wax and mimosa wax.

Non-limiting examples of fatty acids are the same as those described above for the at least one fatty acid described above. This includes carboxylate salts of the fatty acids listed above. The sodium, potassium, ammonium, calcium and magnesium carboxylates of the fatty acids listed above are typical examples of the carboxylate salts of the fatty acids.

Non-limiting example of fatty alcohols include compounds of formula (VI):

R—OH            (VI)

where R is as described above for the at least one fatty acid.

Non-limiting fatty esters include esters formed from the fatty acid of formula (I) and $C_{1-22}$ alcohols and esters formed from the fatty alcohol of formula VI and $C_{1-22}$ carboxylic acids.

In addition, non-limiting specific examples of water-insoluble ingredients includes isopropyl palmitate, capric/caprylic triglyceride, isododecane, polylsobutylene, tocopherol, tocopherol acetate, retinol, retinyl palmitate, 2-oleamido-1,3-octadecanediol, octymethoxy cinnamate, octyl salicylate, 18-methyleicosanoic Acid and mixtures thereof.

The at least one water-insoluble ingredient (c) is present in the composition in a positive amount up to about 50% by weight, typically a positive amount up to about 30% by weight, and more typically a positive amount up to about 15% by weight based on the weight of the composition as a whole. In other embodiments, the at least one water-insoluble ingredient (c) is present in the composition in an amount from about 0.1% to about 50% by weight and in an amount from about 0.5% to about 15% by weight based on the weight of the composition as a whole.

The at least one hair colorant (d) may be selected from any type of colorant commercially available in the hair coloring industry. This includes direct dyes, oxidative dyesazoic dyes, sulfur dyes, azomethine dyes, triarylmethane, xanthene dyes, phthalocyanin dyes, phenothiazine dyes, pigments, direct dyes, oxidation dyes, nacreous pigments, pearling agents, leuco dyes, optical lightening colorants, natural colorants, optically-variable pigments and mixtures thereof. The at least one hair colorant may be present in an amount from to about 0.001% to about 5% by weight, based on the weight of the composition.

Specific non-limiting examples of useful dyes are listed in U.S. Pat. No. 7,141,079, U.S. Pat. No. 7,122,062, U.S. Pat. No. 7,094,262, U.S. Pat. No. 7,083,655, U.S. Pat. No. 6,740,130, U.S. Pat. No. 6,139,853 and U.S. Pat. No. 5,951,718, the contents of which are herein incorporated by reference.

The coloring agent may also comprise a colorant chosen from water-soluble or liposoluble dyes or alternatively coloring polymers. The colorant may be present in the composition in content of coloring active material ranging from 0 to 6% (especially 0.01% to 6%) by weight and typically ranging from 0.01% to 3% by weight relative to the total weight of the composition.

The liposoluble dyes are, for example, soybean oil, Sudan brown, DC Yellow 11, DC Orange 5, quinoline yellow, Sudan Red III (CTFA name D&C red 17), lutein, quinizarine green (CTFA name DC green 6), Alizurol SS purple (CTFA name DC violet No. 2), DC Blue No. 14, carotenoid derivatives, for instance lycopene, beta-carotene, bixin or capsanthin, annatto, and/or mixtures thereof. The liposoluble dyes, when present, generally have a concentration ranging up to 20% by weight of the total weight of the composition. Typically, when present, the liposoluble dyes are present in an amount from about 0.0001% to about 6% by weight, based on the weight of the composition.

Among the water-soluble dyes that may be mentioned are dyeing plant extracts such as, for example, *Aleurites moluccana* Wild, *Alkanna tinctoria* Tausch, *Areca catechu* L., *Arrabidaea chica* E. and B., *Bixa orellana* L (annatto), *Butea monosperma* Lam, *Caesalpina echinata* Lam, *Caesalpina sappan* L., *Calophyllum inophyllum* L., *Carthamus tinctorius* L., *Cassia alata* L., *Chrozophora tinctoria* L., *Crocus sativus* L., *Curcuma longa* L., *Diospyros gilletii* Wild, *Eclipta prostrata* L., *Gardenia erubescens* Stapf and Hutch., *Gardenia terniflora* Schum. and Thonn., *Genipa americana* L., *Genipa brasiliensis* L., *Guibourtia demeusei* (Harms) J. Leon, *Haematoxylon campechianum* L., *Helianthus annuus*, *Humiria balsamifera* (Aubl) St-Hil, *Isatis tinctoria* L., *Mercurialis perenis*, *Monascus purpureus*, *Monascus ruber*, *Monascus pilosus*, *Morus nigra* L., *Picramnia spruceana*, *Pterocarpus erinaceus* Poir., *Pterocarpus soyauxii* Taub., *Rocella tinctoria* L., *Rothmannia whitfieldii* (Lindl) Dand., *Schlegelia violacea* (Aubl) Griseb., *Simira tinctoria* Aublet, *Stereospermum kunthianum* Cham, *Symphonia globulifera* L., *Terminalia catappa* L., sorghum, *Aronia melanocarpa*, naphthoquinones including lawsone, derived from *Lawsonia inermis* L., also known as henna, or from *Impatiens balsamina*, red wood extracts as described in document WO 98/44902, beetroot juice, the disodium salt of suschin, anthocyans, for instance extracts of red berries, dihydroxyacetone, monocarbonyl or polycarbonyl derivatives such as isatin, alloxan, ninhydrin, glyceraldehyde, mesotartaric aldehyde, pyrazoline-4,5-dione derivatives, and mixtures thereof, these skin-coloring agents optionally being combined with direct dyes or indole derivatives, and/or mixtures thereof.

These dyeing plant extracts may be in the form of a lyophilizate, a paste or a solution: generally, the leaves of the dyeing plant are ground to obtain a powder. This powder is dissolved in an aqueous phase for several hours. The mixture is subsequently centrifuged and then filtered. The filtrate obtained is frozen and then lyophilized.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, may be present in the composition in a concentration ranging up to 50% by weight of the total weight of the composition, such as from 0.1% to 20%, preferably from 0.1% to 15%.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, silica, ferric blue, and mixtures thereof. Representative examples of organic pigments include carbon black, pigments of D & C type, and lakes based on cochineal carmine, bariumn strontium, calcium, and aluminum. Other examples of pigments are ultramarines, HC Blue No. 14, Ext. Yellow 7, Yellow 10 Lake, and acid violet 43.

If present, the pigments may be present in the composition in a concentration ranging up to 50% by weight based on the total weight of the composition, such as from about 0.5% to about 40% by weight, and further such as from about 2% to about 30% by weight.

The coloring agent may also comprise a coloring polymer, i.e. a polymer comprising at least one organic coloring group. The coloring polymer generally contains less than 10% by weight of colorant relative to the total weight of the polymer.

The coloring polymer may be of any chemical nature, especially a polyester, polyamide, polyurethane, polyacrylic, poly(meth)acrylic, polycarbonate, polymers of natural origin, for instance cellulose polymers or chitosan polymers, or mixtures thereof, and preferably polyester or polyurethane polymers.

The coloring polymer may comprise a coloring group [lacuna] may be grafted, especially by covalent bonding, onto the polymer chain, as described in documents WO-A-96/29046, WO-A-92/01022, WO-A-90/07558 and BE-A-609 054.

In particular, the coloring polymer may be a copolymer based on at least two different monomers, at least one of which is an organic coloring monomer.

The monomers of the coloring polymer may be chosen from anthraquinones, methines, bis-methines, aza-methines, arylidenes, 3H-dibenzo[7,i-j]isoquinolines, 2,5-diaryllaminoterephthalic acids and esters thereof, phthaloylphenothiazines, phthaloylphenoxazines, phthaloylacridone, anthrapyrimidines, anthrapyrazoles, phthalocyanins, quinophthalones, indophenols, perinones, nitroarylamines, benzodifurans, 2H-1-benzopyran-2-ones, quinophthalones, perylenes, quinacridones, triphenodioxazines, fluoridines, 4-amino-1,8-naphthalimides, thioxanthrones, benzanthrones, indanthrones, indigos, thioindigos, xanthenes, acridines, azines and oxazines.

Coloring monomers are described especially in documents U.S. Pat. No. 4,267,306; U.S. Pat. No. 4,359,570; U.S. Pat. No. 4,403,092, U.S. Pat. No. 4,617,373; U.S. Pat. No. 4,080,355; U.S. Pat. No. 4,740,581; U.S. Pat. No. 4,116,923; U.S. Pat. No. 4,745,173; U.S. Pat. No. 4,804,719; U.S. Pat. No. 5,194,463; U.S. Pat. No. 5,804,719; WO-A-92/07913.

Polymeric colorants are described especially in documents U.S. Pat. No. 4,804,719; U.S. Pat. No. 5,032,670; U.S. Pat. No. 4,999,418; U.S. Pat. No. 5,106,942; U.S. Pat. No. 5,030,708; U.S. Pat. No. 5,102,980; U.S. Pat. No. 5,043,376; U.S. Pat. No. 5,194,463; WO-A-92/07913; WO-A-97/24102, the content of which is incorporated into the present patent application by reference.

Sulphopolyester coloring-polymers such as those described in document WO-A-97/24102 are typically used.

The coloring polymers may be present in the composition according to the disclosure in a content ranging from about 0.01% to about 50% typically ranging from about 0.5% to about 25% by weight and more typically ranging from about 0.2% to about 20% by weight relative to the total weight of the composition.

The at least one hair colorant (d) may also be selected from any type of bleach commercially available in the hair bleaching industry. Bleaching agents include, but not limited to, hydrogen peroxide, perborate and persufate salts such as sodium, potassium, or ammonium salts of perfulfates or perborates. When used, the bleach is present in an amount of from about 0.001% to about 95% by weight, based on the weight of the composition.

Solvent (e) in the composition is present in an amount from about 10% by weight to about 95% by weight, typically in an amount from about 50% by weight to about 85% by weight and more typically from about 60% by weight to 80% by weight, based on the weight of the composition as a whole. The solvent is typically water, alcohol, glycol or mixtures thereof. Alcohols include ethanol, propanol and butanol. Typically, the alcohol is ethanol or isopropanol. Glycols include hexylene glycol, diethylene glycol, ethylene glycol, propylene glycol, 1,2-butylene glycol, triethylene glycol, dipropylene glycol, and mixtures thereof.

The composition may optionally contain at least one auxiliary ingredient (f) in a positive amount up to about 50% by weight based on the composition. The auxiliary ingredient may include an amino acid, a protein, a cationic conditioner, a cationic polymer, a anionic surfactant, a nonionic surfactant, a amphoteric surfactant, a zwitterionic surfactant, a viscosity modifier, an organosiloxane polymer, a wax, a silicone resin, a pigment, a powder, a preservative, an antioxidant, a vitamin, an alpha hydroxy acid, a beta hydroxy acid, an alpha ketoacid, an antibacterial agent, a sunscreen, a preservative, a pH adjusting agent, a bleaching agent, a perfume, a sequestering agent, an anti-dandruff agent and mixtures thereof.

EDTA and other aminocarboxylates may be used as sequestering agents.

Anti-dandruff agents such as zinc pyrithione, salicylic acid, climbazole, ketoconazole, sulfur piroctone olamine, selenium sulfide and mixtures thereof may also be used as an auxiliary ingredient.

Non-limiting examples of proteins include collagen, deoxyribonuclease, iodized corn protein, milk protein, protease, serum protein, silk, sweet almond protein, wheat germ protein, wheat protein, alpha and beta helix of keratin proteins, hair proteins, such as intermediate filament proteins, high-sulfur proteins, ultrahigh-sulfur proteins, intermediate filament-associated proteins, high-tyrosine proteins, high-glycine tyrosine proteins, tricohyalin, and mixtures thereof.

Non-limiting examples of amino acids include amino acids derived from the hydrolysis of various proteins as well as the salts, esters, and acyl derivatives thereof. Non-limiting examples of such amino acid agents include amphoteric amino acids such as alkylamido alkylamines, i.e. stearyl acetyl glutamate, caproyl silk amino acid, caproyl collagen amino acids, caproyl keratin amino acids, caproyl pea amino acids, cocodimonium hydroxypropyl silk amino acids, corn gluten amino acids, cysteine, glutamic acid, glycine, hair keratin amino acids, amino acids such as asparatic acid, threonine, serine, glutamic acid, proline, glycine, alanine, cystine, valine, methionine, isoleucine, leucine, tyrosine, phenylalanine, cysteic acid, lysine, histidine, arginine, cysteine, tryptophan, citrulline, lysine, silk amino acids, wheat amino acids and mixtures thereof.

Non-limiting examples of cationic conditioners include quaternium-27, behenamidopropyl PG-dimonium chloride, hydroxyethyl tallowdimonium chloride, hexadimethrine chloride, stearalkonium chloride and cetrimonium chloride.

Conditioning agents may be chosen from amino acids, proteins, extracts, fats, oils, esters, transesters, hydrocarbons, quats, polyquats, zwitterionic surfactants, amphoteric surfactants, alcohols, polyols, humectants, alkanolamides, fatty acids, ketones, and mixtures thereof. The conditioning agent is present in an amount from about 0.001% to about 50% by weight, based on the weight of the composition. Typically, the conditioning agent is present in an amount from about 0.1% to about 35% by weight, based on the weight of the composition and more typically in an amount from about 1% to about 20% by weight, based on the weight of the composition.

Non-limiting examples of conditioning agents include Arginine, Asparagine, Aspartic Acid, Carnitine, Cocoyl sarcosine, Glycine, Glutamic acid, Histidine, Hydroxyproline, Acetyl Hydroxy praline, Isoleucine, Lysine, Lauroyl Lysine, Lauroyl Sarcosine, Methionine, Phenylalanine, Polylysine, Potassium Cocoyl Glutamate, Proline, Sarcosine, Serine, Rice amino acids, Silk amino acids, Wheat amino aids, Sodium Glutamate, Sodium Lauroyl Glutamate, Sodium PCA, Stearoyl sarcosine, Threonine, Tyrosine, Tryptophan, Valine, Casein, Collagen, Procollagen, Gelatin, Keratin, Glycoproteins, Hydrolyzed wheat protein, Hydrolyzed soy protein, Hydrolyzed oat protein, Hydrolyzed rice protein, Hydrolzed vegetable protein, Hydrolyzed yeast protein, Whey protein, *Ginkgo Biloba* Nut extract, *Salix Alba* (Willow) Bark Extract, *Morus Alba* (Mulberry) Leaf, Behentrimonium Chloride, Behenamidopropyl PG-Dimonium Chloride, Behentrimonium Methosulfate, Cocotrimonium Methosulfate, Olealkonium Chloride, Steartrimonium Chloride, Babassuamidopropalkonium Chloride, Hydroxypropyl Guar, Hydroxypropyltrimonium chloride, Laurdimonium Hydroxypropyl Hydrolyzed Soy Protein, Steardimonium Hydroxypropyl Hydrolyzed Wheat Protein, Quaternium-22, Quaternium-27, Quaternium-87, Polyquaternium-4, Polyquaternium-6, Polyquaternium-10, Polyquaternium-11, Polyquaternium-44, Polyquaternium-67, Silicone Quaterium-8, Amodimethicone, Aminopropyldimethicone, Phenyltrimethicone, Cyclomethicone, Dimethicone, Hexyl Dimethicone, Dilinoleamidopropyl Dimthylamine Dimethicone PEG-7 Phosphate, C26-28 Alkyl Dimethicone, PEG-8 Dimethicone, PPG-12 Dimethicone, Polysilicone-13, Trideceth-9 PG-Amodimethicone, Bis-PEG-12 Dimethicone Beeswax, Capric/Caprylic Triglyceride, Petrolatum, Mineral Oil, Lanolin Oil, *Cocos nucifera* (Coconut) Oil, *Olea Europea* (Olive) Fruit Oil, *Simmondsia Chinensis* (Jojoba) Seed Oil, *Prunus Armeniaca* (Apricot) Kernel Oil, *Crambe Abyssinica* Seed Oil, Vegetable Oil, *Zea Mays* (Corn) Oil, Acetylated Lanolin Alcohol, Cetearyl Isononanoate, Cetearyl Ethylhexanoate, Cetearyl Palmitate, Hydrogenated Olive Oil Hexyl Esters, Triethylhexanoin, Ceramide-3, Caprylyl Glycol, Cetyl Glycol, Glycerin, Panthenol, Phytantriol, Methanediol, Inositol, PPG-35-Buteth-45, PPG-5 Butyl Ether, Cocoamidopropyl Betaine, Coco-Betaine, Cocoamidopropyl Hydroxysultaine, Lauramidopropyl Betaine, Lauryl Betaine, Oleamidopropyl Betaine, Disodium Cocoamphodiacetate, Disodium Cocoamphodipropionate, Disodium Lauroamphodiacetate, Sodium Cocoamphopropionate, Sodium Cocoamphoacetate, Acetamide MEA, Behenamide MEA, Linoleamide DEA, Linoleamide MEA, Linoleamide MIPA, Linoleic Acid, Linolenic Acid, Maltodextrin, Niacin, Polyacrylate-1 Crosspolymer, Polyester-4, Pyridoxine HCl, Phytosphingosine, Salicylic Acid, Squalane, Squalene, Thiodiglycoamide, Zinc Pyrithione, and mixtures thereof.

Non-limiting examples of cationic polymers include polyquaternium-4, polyquaternium-6, polyquaternium-7, polyquaternium-10, polyquaternium-11, polyquaternium-16, polyquaternium-22 and polyquaternium-32.

Non-limiting examples of nonionic surfactants includes alkoxylated derivatives of the following: fatty alcohols, alkyl phenols, fatty acids, fatty acid esters and fatty acid amides, wherein the alkyl chain is in the $C_{12-50}$ range, typically in the $C_{16-40}$ range, more typically in the $C_{24}$ to $C_{40}$ range, and having from about 1 to about 110 alkoxy groups. The alkoxy groups are selected from the group consisting of $C_2$-$C_6$ oxides and their mixtures, with ethylene oxide, propylene oxide, and their mixtures being the typical alkoxides. The alkyl chain may be linear, branched, saturated, or unsaturated. Of these alkoxylated non-ionic surfactants, the alkoxylated alcohols are typical, and the ethoxylated alcohols and propoxylated alcohols are more typical. The alkoxylated alcohols may be used alone or in mixtures with those alkoxylated materials disclosed herein-above.

Other representative examples of such ethoxylated fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10), steareth-10 (a stearyl alcohol ethoxylate having an average degree of ethoxylation of 10), steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and other derivatives and mixtures of the preceding.

Commercially available nonionic surfactants are Brij® nonionic surfactants from Uniqema, Wilmington, Del. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij 72 (i.e., Steareth-2) and Brij 76 (i.e., Steareth-10).

Also useful herein as nonionic surfactants are alkyl glycosides, which are the condensation products of long chain alcohols, which are the condensation products of long chain alcohols, e.g. $C_8$-$C_{30}$ alcohols, with sugar or starch polymers. These compounds can be represented by the formula (S)n-O—R wherein S is a sugar moiety such as glucose, fructose, mannose, galactose, and the like; n is an integer of from about 1 to about 1000, and R is a $C_8$-$C_{30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a $C_8$-$C_{20}$ alkyl group, and n is an integer of from about 1 to about 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein sucrose ester surfactants such as sucrose cocoate and sucrose laurate.

Other nonionic surfactants suitable for use in the present invention are glyceryl esters and polyglyceryl esters, including but not limited to, glyceryl monoesters, typically glyceryl monoesters of $C_{16}$-$C_{22}$ saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of $C_{16}$-$C_{22}$ saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of $C_{16}$-$C_{22}$ saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from Uniqema, Wilmington, Del.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Also suitable for use as nonionic surfactants are alkoxylated derivatives of glyceryl esters, sorbitan esters, and alkyl polyglycosides, wherein the alkoxy groups is selected from the group consisting of $C_2$-$C_6$ oxides and their mixtures, with ethoxylated or propoxylated derivatives of these materials being typical. Non-limiting examples of commercially available ethoxylated materials include TWEEN® (ethoxylated sorbitan mono-, di- and/or tri-esters of $C_{12}$ to $C_{18}$ fatty acids with an average degree of ethoxylation of from about 2 to 20).

Non-limiting examples of anionic surfactants include compounds in the classes known as alkyl sulfates, alkyl ether sulfates, alkyl sulfonates, alkyl ether sulfonates, sulfate esters of an alkylphenoxy polyoxyethylene ethanol, alpha-olefin sulfonates, beta alkyloxy alkene sulfonates, alkyl arylsulfonates, alkyl carbonates, alkyl ether carboxylates, fatty acids, succinamates, sulfosuccinates, sarcosinates, octoxynol or nonoxynol phosphates, taurates, fatty taurides, sulfated monoglycerides, fatty acid amino polyoxyethylene sulfates, isothienates and mixtures thereof. Specific examples of anionic surfactants include the ammonium, monoethanolamine, diethanolamine, triethanolamine, isopropylamine, sodium, potassium, lithium, or magnesium salts of lauryl sulfate, dodecylbenzene-sulfonate, lauryl sulfosuccinate, lauryl ether sulfate, lauryl ether carboxylate, lauryl sarcosinate, cocomethyl tauride, and sulfosuccinate half ester amide and mixtures thereof.

Non-limiting examples of amphoteric and zwitterionic surfactants include alkyl, alkyl dimethyl, alkylamido, alkyl amide, alkylamidopropyl, or alkyl dimethylammonium betaine; alkyl amidopropyl or alkyl sulfobetaine; alkyl, alkylampho, or alkylamphocarboxy glycinate; alkyl, or alkyl substituted imidazoline mono or dicarboxylate; sodium salts of alkyl mono- or dicarboxylates; alkyl beta amino acids; alkyl amidopropyl, or alkyl ether hydroxysultaine; alkyl amidopropyl dimethyl ammonia acetate; alkyl ampho mono- or diacetate; alkyl, or alkyl ampho, or alkyl imino dipropionate; alkyl amphopropionate; alkyl beta amino propionic acid; alkyl dipropionate; alkyl beta iminodipropionate; branched or n-alkyl dimethylamidopropionate; alkyl carboxylated propionate; alkyl, or methyl alkyl imidazoline; fluorinated alkyl amphoteric mixtures; and/or nonionic surfactants such as, but not limited to, alkyl, alkyl dimethyl, alkyl amidopropylamine, or bis 2-hydroxy ethyl alkyl amine oxides; alkanolamides; alkyl amides; polyoxyethylene glycol (PEG) of monoglycerides, of sorbitan esters, of branched or linear fatty alcohol ethers, of branched or linear fatty acid ethers, of thioethers; alkyl oxoalcohol PEG; PEG fatty esters; polyoxyethlyene glycol/polyoxpropylene glycol block copolymers; alkyl phenol PEG ethers; alkyl polyglucosides, or polysaccharides, polysiloxane polyethoxylene ether and mixtures thereof.

Specific examples include cocamidopropyl betaine, lauramidopropyl betaine, coco/oleamidopropyl betaine, lauryl betaine, coco betaine, oleyl betaine, cocamidopropyl hydroxysultaine, tallowamidopropyl hydroxysultaine, dihydroxyethyl tallow glycinate, disodium cocoamphodiacetate, disodium cocoamphodipropionate and mixtures thereof.

Non-limiting examples of viscosity modifiers include water swellable/soluble cationic polymers from quaternized polysaccharides such as trimethyl ammonium substituted epoxide of hydroxyethyl cellulose, diallyl dimethyl ammonium salts of hydroxyethylcellulose, deacylated chitin or chitosan, dihydroxypropyl chitosan trimonium chloride, hydroxypropltrimethyl ammonium chloride guar, locust bean, or konjac mannan gum; quaternized synthetics such as acrylamide dimethyl diallyl ammonium chloride copolymers, acrylamide/dimethyl diallyl ammonium chloride/acrylic acid terpolymer, quaternized poly(vinyl pyrrolidone/dimethyl amino ethylmethacrylate), poly(vinylpyrrolidone/methacrylamidopropyl trimethylammonium chloride), polyvinyl pyrrolidone/methylvinylimidazolinium chloride or methyl sulfate copolymer, chloroethylether/dimethylaminopropylamine/adipate or azelate terpolymer, vinylpyrrolidone/methacrylamidopropyl trimethylammonium chloride, acrylonitrile/acrylic acid/dimethylpropanediammonium acrylates sulfate terpolymer. Anionic or nonionic polysaccharide polymers such as gum tragacanth, sodium or propylene glycol alginate, kappa-, iota-, or lambda-carrageenan, guar or hydroxyl propyl guar gum, karaya gum, gum Arabic, locust bean gum, konjac mannan gum, gellan, xanthan, succinoglycan or its acidic or enzymatic hydrolysates, sodium carboxymethyl cellulose, methylcellulose, hydroxyethylcellulose, hydroxypropylmethylcellulose, and hydroxypropylecellulose; and/or hydrophobically modified anionic, cationic, or nonionic polymers such as, but not limited to, alkyl and/or substituted hydroxyethylcellulose, lauryl dimethyl ammonium substituted epoxide of hydroxyethylcellulose, propoxylated cellulosic, xanthan, succinoglycan, or polygalactomannoses, alkyl methacrylates/crosslinked acrylic acid copolymer and/or acrylonitrile/acrylates block copolymer.

Examples of organosiloxane polymers useful in the disclosure are commercially available from Goldschmidt Corporation under the ABIL tradename. One typical example is cetyl dimethicone copolyol and has the tradename ABIL WE 09 or ABIL WS 08. The cetyl dimethicone copolyol may be used alone or in conjunction with other non-silicone organic emulsifiers. For example, the cetyl dimethicone copolyol may be used in an admixture with other non-silicone organic auxiliary ingredients such a emulsifiers and emollients. For example, the mixtures identified by the C.T.F.A. names cetyl dimethicone copolyol (and) polyglyceryl 4-isostearate (and) hexyl laurate, or cetyl dimethicone copolyol (and) polyglyceryl-3 oleate (and) hexyl laurate both work well. These blends contain approximately 25-50% of each ingredient, for example ABIL WE 09 contains approximately, by weight of the total ABIL composition, 25-50% cetyl dimethicone copolyol, 25-50%, polyglyceryl 4-isostearate, and 25-50% of hexyl laurate which is an emollient or oil.

Another type of organosiloxane polymer suitable for use in the compositions of the disclosure are sold by Union Carbide under the Silwet™ trademark. These compositions are represented by the following generic formulas:

$(Me_3Si)_y$-2$[(OSiMe_2)_x$/yO-PE$]_y$ wherein PE=-$(EO)_m(PO)_n$R

R=lower alkyl or hydrogen

Me=methyl

EO is polyethyleneoxy

PO is polypropyleneoxy m and n are each independently 1-5000 x and y are each independently 0-5000, and 8 wherein PE=—CH$_2$CH$_2$CH$_2$O(EO)$_m$(PO)$_n$Z
Z=lower alkyl or hydrogen, and
Me, m, n, x, y, EO and PO are as described above,
with the proviso that the molecule contains a lipophilic portion and a hydrophilic portion. Again, the lipophilic portion can be supplied by a sufficient number of methyl groups on the polymer backbone.

Examples of other polymeric organosiloxane surfactants or emulsifiers include amino/polyoxyalkyleneated polydiorganosiloxanes disclosed in U.S. Pat. No. 5,147,578. Also suitable are organosiloxanes sold by Goldschmidt under the ABIL trademark including ABIL B-9806, as well as those sold by Rhone-Poulenc under the Alkasil tradename. Also, organosiloxane polymers sold by Amerchol under the Amersil tradename, including Amersil ME-358, Amersil DMC-287 and Amersil DMC-357 are suitable. Dow Corning surfactants such as Dow Corning 3225C Formulation Aid, Dow Corning 190 Surfactant, Dow Corning 193 Surfactant, Dow Corning Q2-5200, and the like are also suitable. In addition, products sold under the tradename Silwet by Union Carbide, and products sold by Troy Corporation under the Troysol tradename, those sold by Taiwan Surfactant Co. under the tradename Ablusoft, those sold by Hoechst under the tradename Arkophob, are also suitable for use in the disclosure.

The compositions of the disclosure may contain wax at a concentration about 0.1-25%, preferably 0.5-20%, more typically 1-15% by weight based on the total weight of the composition. Suitable waxes have a melting point of 35 to 120° C., and can be animal waxes, plant waxes, mineral waxes, silicone waxes, synthetic waxes, and petroleum waxes. Examples of waxes in accordance with the disclosure include bayberry, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, ozokerite, paraffin, PEG-6 beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, ethylene homo- or copolymers, stearoxy dimethicone, dimethicone behenate, stearyl dimethicone, and the like, as well synthetic homo- and copolymer waxes such as PVP/eicosene copolymer, PVP/hexadecene copolymer, and the like.

Silicone resins in the compositions of the disclosure may be added at a concentration in a range of about 0.001-20%, typically 0.01-15%, more typically 0.1-10% by weight based on the total weight of the composition. Examples of suitable silicone resins include siloxy silicate polymers having the following general formula:

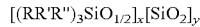

wherein R, R' and R" are each independently a C$_{1-10}$ straight or branched chain alkyl or phenyl, and x and y are such that the ratio of (RR'R")$_3$SiO$_{1/2}$ units to SiO$_2$ units is 0.5 to 1 to 1.5 to 1.

Typically R, R' and R" are a C$_{1-6}$ alkyl, and more preferably are methyl and x and y are such that the ratio of (CH$_3$)$_3$SiO$_{1/2}$ units to SiO$_2$ units is 0.75 to 1. For example, a trimethylsiloxy silicate containing 2.4 to 2.9 weight percent hydroxyl groups which is formed by the reaction of the sodium salt of silicic acid, chlorotrimethylsilane, and isopropyl alcohol may be used. The manufacture of trimethylsiloxy silicate is set forth in U.S. Pat. Nos. 2,676,182; 3,541,205; and 3,836,437, all of which are hereby incorporated by reference. Trimethylsiloxy silicate as described is available from Dow Corning Corporation under the tradename 2-0749 and 2-0747, which is a blend of about 40-60% volatile silicone and 40-60% trimethylsiloxy silicate. Dow Corning 2-0749 in particular, is a fluid containing about 50% trimethylsiloxy silicate and about 50% cyclomethicone. The fluid has a viscosity of 200-700 centipoise at 25° C., a specific gravity of 1.00 to 1.10 at 25° C., and a refractive index of 1.40-1.41.

Other silicone resins are silicone esters comprising units of the general formula R$_a$R$^E_b$SiO$_{[4-(a+b)/2]}$ or R$^{13}_x$R$^E_y$SiO$_{1/2}$, wherein R and R$^{13}$ are each independently an organic radical such as alkyl, cycloalkyl, or aryl, or, for example, methyl, ethyl, propyl, hexyl, octyl, decyl, aryl, cyclohexyl, and the like. a is a number ranging from 0 to 3, b is a number ranging from 0 to 3, a+b is a number ranging from 1 to 3, x is a number from 0 to 3, y is a number from 0 to 3 and the sum of x+y is 3, and wherein R$^E$ is a carboxylic ester containing radical. Typical R$^E$ radicals are those wherein the ester group is formed of one or more fatty acid moieities (e.g. of about 6, often about 6 to 30 carbon atoms) and one or more aliphatic alcohol moieities (e.g. of about 10 to 30 carbon atoms). Examples of such acid moieities include those derived from branched-chain fatty acids such as isostearic, or straight chain fatty acids such as behenic. Examples of suitable alcohol moieties include those derived from monohydric or polyhydric alcohols, e.g. normal alkanols such as n-propanol and branched-chain etheralkanols such as (3,3,3-trimethylolpropoxypropane. Typically, the ester subgroup (i.e. the group containing the carboxylic ester) will be linked to the silicon atom by a divalent aliphatic chain that is at least 2 or 3 carbon atoms in length, e.g. an alkylene group or a divalent alkyl ether group. Most typically, that chain will be part of the alcohol moiety, not the acid moiety. More typically, the cross-linked silicone ester can be a liquid or solid at room temperature. The compound may have a waxy feel and a molecular weight of no more than about 100,000 daltons.

Such silicone resins having the above formula are disclosed in U.S. Pat. No. 4,725,658 and U.S. Pat. No. 5,334,737, which are hereby incorporated by reference. These ingredients are commercially available from General Electric under the tradenames SF 1318 and SF 1312, respectively.

Pigments and powder may be added as a auxiliary ingredient at a concentration of about 0.001-35%, typically 0.01-20%, more typically 0.1-10%, by weight based the total weight of the composition. Typically the pigments and powders have a particle size of 0.02 to 200 microns, typically 0.5 to 100 microns. The particulate matter may be colored or non-colored (for example white). Suitable powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone oil or various other agents either alone or in combination, which coat the powder surface and render the particles more lipophilic in nature.

The powder component also may comprise various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof.

The auxiliary ingredient may contain a mixture of both pigmented and non-pigmented powders. The percentage of pigments used in the powder component will depend on the type of cosmetic being formulated.

The auxiliary ingredient of the disclosure may contain 0.001-20%, typically 0.01-10%, more typically 0.05-8% of one or more sunscreens. A sunscreen is defined as an ingredient that absorbs at least 85 percent of the light in the UV range at wavelengths from 290 to 320 nanometers, but transmit UV light at wavelengths longer than 320 nanometers. Sunscreens generally work in one of two ways. Particulate materials, such as zinc oxide or titanium dioxide, as mentioned above, physically block ultraviolet radiation. Chemical sunscreens, on the other hand, operate by chemically reacting upon exposure to UV radiation. Suitable sunscreens that may be included in the compositions of the invention are set forth on page 582 of the CTFA Cosmetic Ingredient Handbook, Second Edition, 1992, as well as U.S. Pat. No. 5,620,965, both of which are hereby incorporated by reference. Examples of such sunscreen materials are p-aminobenzoic acid (PABA), cinoxate, diethanolamine p-methoxycinnamate (DEA-methoxycinnamate), Digalloyl trioleate, dioxybenzone (Benzophenone-8), ethyl 4-[bis-(hydroxypropyl)]aminobenzoate(ethyl dihydroxypropyl PABA), 2-ethythexyl-2-cyano-3,3-diphenylacrylate(octocrylene), ethylhexyl p-methoxycinnamate (Octyl methoxycinnamate), 2-ethylhexyl salicylate (Octyl salicylate), glyceryl aminobenzoate (Glyceryl PABA), homosalate, lawsone with dihydroxyacetone, menthyl anthranilate, oxybenzone (Benzophenone-3), Padimate A (Pentyl Dimethyl PABA), (Octyl Dimethyl PABA), 2-Phenylbenzimidazole-5-sulfonic acid (Phenylbenzimidazole Sulfonic acid), Red Petrolatum, Sulisobenzone (Benzophenone4), triethanolamine salicylate (TEA-Salicylates), benzophenones, bornelone, butyl PABA, cinnamidopropyl trimethyl ammonium chloride, disodium distyrylbiphenyl disulfonate, PABA, potassium methoxycinnamate, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, Padimate O and mixtures thereof.

The auxiliary ingredient may include about 0.0001-8%, typically 0.001-6%, more typically 0.005-5% by weight of a preservative based on the total weight of the composition. A variety of preservatives are suitable, including such as benzoic acid, benzyl alcohol, ethanol, polyvinyl alcohol, phenoxyethanol, methyl paraben, propyl paraben, benzylhemiformal, benzylparaben, 5-bromo-5-nitro-1,3-dioxane, 2-bromo-2-nitropropane-1,3-diol, butyl paraben, calcium benzoate, calcium propionate, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and all of those disclosed on pages 570 to 571 of the CTFA Cosmetic Ingredient Handbook, Second Edition, 1992, which is hereby incorporated by reference. The auxiliary ingredient may include mixtures of these preservatives.

The auxiliary ingredient of the disclosure may contain vitamins and/or coenzymes, as well as antioxidants. These may be added at a concentration of about 0.001-10%, typically 0.01-8%, more typically 0.05-5% by weight based on the total weight of the composition. Suitable vitamins include the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and mixtures thereof.

The auxiliary ingredient may include one or more alpha or beta hydroxy acids or alpha ketoacids. Typical ranges are 0.01-20%, more typically 0.1-15%, and even more typical 0.5-10% by weight based on the total composition. Suitable alpha hydroxy acids and alpha ketoacids are disclosed in U.S. Pat. No. 5,091,171, which is hereby incorporated by reference. The general structure of such alpha hydroxy acids may be represented by the following formula:

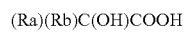

(Ra)(Rb)C(OH)COOH wherein Ra and Rb are H, F, Cl, Br, alkyl, aralkyl, or aryl group of saturated, unsaturated, straight or branched chain or cyclic form having 1-10 carbon atoms, and in addition Ra or Rb may carry OH, CHO, COOH and alkoxy groups having 1 to 9 carbon atoms.

The alpha hydroxy acids may exist in the keto acid form, or the ester form. Examples of such alpha hydroxy acids include glycolic acid, malic acid, pyruvic acid, mandelic acid, lactic acid, methyllactic acid, and mixtures thereof.

Also beta hydroxy acids such as salicylic acid, and derivatives thereof may be included in the compositions of the disclosure. In addition, mixtures of the above alpha and beta hydroxyl acids or alpha ketoacids.

Non-limiting examples of antibacterial agents include bacitracin, phenol, benzethonium chloride, erythromycin, neomycin, tetracycline, chlortetracycline and mixtures thereof.

Non-limiting examples of pH adjusting agents includes potassium acetate, sodium carbonate, sodium hydroxide, phosphoric acid, succinic acid, sodium citrate, citric acid, boric acid, lactic acid, sodium hydrogen carbonate and mixtures thereof.

The following examples are for illustrative purposes only and are not intended to limit the scope of the claims. In the following examples, Lupasol® G-35 is 50% active and Carbopol® Aqua CC is 20% active.

Determination of the Amine Number and the Acid Number

The measurement of the Acid and the Amine Value is performed through a common acid-base titration in the presence of a color indicator. The method is based on the European and American Pharmacopoeias and Standard ISO 660.

Specifically, the acid value measures the quantity of free acid functions titratable with NaOH using Phenolphthalein as an indicator (the endpoint is determined by the slight pink color that persists for at least 15 seconds), and is reported as milliequivalent of acid per grams (meq/g) of the acid substance.

Similarly, the amine value measures the quantity of amine functions titratable with HCl using Bromophenol Blue as an indicator (the endpoint is determined by the slight blue color that persists for at least 15 seconds), and is reported as milliequivalent of amine per gram (meq/g) of the polyamine.

General Procedure for Combining Components of the Disclosure

The at least one acid, at least one water-insoluble ingredient and other optional oil-based ingredients are mixed at a temperature of at least 25° C. in a container A. The at least one polyamine, water and other optional ingredients are mixed at a temperature of at least 25° C. in a container B. Next the contents of container B is slowly added to container A with high shear mixing. After all of container B is added, other optional ingredients described above are added while mixing at high shear. Mixing continues until a homogeneous mixture is obtained. Coloring agents (d), additional solvent (e) and optional component (f) may be mixed with the composition if the coloring agent is applied to hair with all the components of the disclosure. Otherwise, the coloring agents (e), additional solvent (e) and optional component (f) may be applied to hair separately either before or after the other components of the disclosure.

1. Water-Resistant Properties of Disclosed Composition

A. General Test for the Measurement of the Water-Resistance of Disclosed Composition The water-resistance of a surface treated with the disclosed composition can be measured using a Contact Angle Measurement System K-12 manufactured by Kruss (Germany). This instrument allows one to calculate the degree of water-resistance of a solid surface when it was pushed in and pulled out of water by measuring the angle formed by the water-solid interface. The low contact angle denotes a low water-resistance (water spreads on the surface), and the high contact angle denotes a high water-resistance (water beads on the surface).

In this test, a microscope cover glass (Fisher brand 12-542A, 18 cm×18 cm×0.16 mm) was treated with a solution of the disclosed composition (50 g of Isopropanol (IPA)+ 10 g of the disclosed composition) by dipping the cover glass to half of its length into the testing solution and allowing it to dry. The treated cover glass is then mounted on the Kruss instrument and the Advancing Contact Angle (Wetting Contact Angle)/Receding Contact Angle (De-wetting Contact Angle) measured using the following parameters:

Measuring Speed: 3 mm/min
Max Immersion Depth: 5 mm
Min Immersion Depth: 0 mm
Sensitivity: 0.01 g B. Measurements of Contact Angle for Mixtures Containing Components (a), (b), (c) and (e)

Following the General procedure described in this above, the Contact Angle of the following compositions were measured (n=5) (Table 1-1):

TABLE 1-1

| IPA (%) | Oleic Acid (%) | Lupasol® G35 (%) | Mineral Oil (%) | Procetyl AWS (%) | Amine #:Acid # | Advancing Contact Angle (°) | Receding Contact Angle (°) |
|---|---|---|---|---|---|---|---|
| 98.08 | 1.04 | 0.38 | 0.5 | — | 1:1 | 92.6 ± 0.6 | 70.7 ± 0.6 |
| 99.87 | 0.10 | 0.016 | 0.008 | — | 1:0.2 | 81.9 ± 1.4 | 65.4 ± 1.7 |
| 88.08 | 1.04 | 0.38 | 0.5 | 10 | 1:1 | 74.0 ± 2.2 | 63.9 ± 0.4 |

The data in Table 1-1 show that when the concentration of the ingredients in the disclosed composition is lowered and the Amine number:Acid number is outside the claimed range, both the Advancing Contact Angle and the Receding Contact Angle decrease to below 66 degrees. A decrease in the contact angle can also be seen in a case where additional ingredients such as nonionic surfactant (Procetyl AWS) are added to the claimed composition. These results demonstrate that not all compositions necessarily have the disclosed contact angle of 66 degrees.

Table 1-2 lists the contact angles on an untreated and a disclosed composition treated glass surface (n=10):

TABLE 1-2

| Tested Disclosed Compositions | | | | | | | |
|---|---|---|---|---|---|---|---|
| Isostearic Acid (%) | Lupasol ® G35 (%) | Ratio of amine number to acid number | Min. Oil (%) | Water (%) | IPA (%) | Contact Angle (°) Advancing | Receding |
| | | | | | 100 | 9.8 ± 2.9 | 6.7 ± 1.6 |
| 0.3 | 0.13 | 1:0.84 | 0.1 | 16.47 | 83.0 | 69.1 ± 1.0 | 66.4 ± 0.3 |
| 1.5 | 0.13 | 1:4.19 | 0.1 | 15.27 | 83.0 | 91.5 ± 1.1 | 73.4 ± 1.8 |
| 5.0 | 1.0 | 1:1.81 | 2.0 | 9.0 | 83.0 | 94.4 ± 1.0 | 73.5 ± 0.6 |

The data demonstrate a significant increase in water-resistance of the glass surface upon treating with the disclosed composition as evidenced by the increase in both the Advancing Contact Angle and the Receding Contact Angle.

C. Water-Resistance of Hair Treated with the Disclosed Composition

Bleached hair (from IHIP, New York) was treated with various shampoo formulas containing the disclosed composition six times (1 g shampoo/g hair, 1 cycle=1 minute shampoo, 30 second rinse). The contact angles between water and the single hair fiber (n=12) were measured. The results are shown in the following Table (Table 1-3):

TABLE 2-1

| Control | % | Test | % |
|---|---|---|---|
| DI Water | 67.8 | DI Water | 66.32 |
| C1. Orange pigment | 10 | C1. Orange pigment | 10 |
| MEA | 22 | Lupasol ® G35 | 3.68 |
| Oleic Acid | 10 | Oleic Acid | 10 |
| Mineral Oil | 10 | Mineral Oil | 10 |
| | | (The ratio of amine number to acid number is 1:1) | |

TABLE 1-3

| Shampoo Containing Disclosed Composition (qs with water) | | | | | | | |
|---|---|---|---|---|---|---|---|
| SLES[1] (%) | Cocamidopropyl Betaine (%) | Fatty Acid (%) | Polyamine (%) | Water-Insoluble Ingredients (%) | Ratio of Amine # to Acid # | Contact Angle (°) Advancing | Receding |
| 7 | 3 | — | — | — | — | 65.61 ± 4.83 | 0.04 ± 0.12 |
| 7 | 3 | Isostearic Acid (0.5) | Lupasol ® G35 (0.4) | Min Oil (0.5) | 1:0.91 | 60.39 ± 2.91 | 38.60 ± 4.53 |
| 7 | 3 | Oleic Acid (0.5) | Carbopol ® aqua CC) (0.75) | Min Oil (1.0) | 1:1.05 | 55.06 ± 3.77 | 12.84 ± 11.02 |
| 7 | 3 | Oleic Acid (2.5) | Carbopol ® aqua CC) (0.75) | Dow Corning ® 200 Fluid 60K (0.75) | 1:5.24 | 58.48 ± 3.94 | 35.10 ± 7.43 |

[1]sodium laureth sulfate

The data shows that hair shampooed with the disclosed composition containing shampoo is water-proof as indicated by the increase in the Receding Contact Angle.

2. Non-chemical Hair Color Intensifier Study Using the Disclosed Composition with Pigment Objective:

To study the initial intensity of color using the disclosed composition with pigment on bleached hair dyed black by a spectrophotometer.

Procedure:

Measure color (baseline) of black hair swatch with spectrophotometer.

Apply 1.8 g of products (Table 2-1) on each swatch (0.7 g:1 g hair). Massage in.

Measure final color.

Calculate % ΔE.

Results:

After applying the product, hair treated with the test formula (disclosed composition with pigment) was significantly more intense in color (% ΔE=32.9) than the hair treated with the control formula (% ΔE=21.9) (traditional soap with pigment).

3. Chemical Hair Color Intensifier Study Using the Disclosed Composition in Chromatic Dye Objective:

To study the color intensifying effect of the disclosed composition mixed into chromatic dye, using a spectrophotometer.

Procedure:

Platinum bleached hair was colored with: (1) the disclosed compositions (Test A-D in Table 3-1) mixed into Prizms® Zappy Red containing Chromatic Dyes, and (2) the Prizms® Zappy Red only (Control).

TABLE 3-1

| Test A | % | Test B | % | Test C | % | Test D | % |
|---|---|---|---|---|---|---|---|
| DI Water | 66 | DI Water | 25 | DI Water | 10.7 | DI Water | 38 |
| Lupasol ® G35 | 4 | Carbopol ® Aqua CC | 20 | Carbopol ® Aqua CC | 34.3 | Amodimethicone | 22 |
| Isostearic Acid | 20 | Isostearic Acid | 25 | Linoleic Acid | 25 | Isostearic Acid | 10 |
| Mineral Oil | 30 | Mineral Oil | 30 | Mineral Oil | 30 | Isopropyl Palmitate | 30 |

Measure color with spectrophotometer.

Results:

Hair colored with the dye containing the disclosed composition (Test A-D) was significantly more intense in color than the hair dyed with the dye alone (Control). Table 3-2 shows the L Value of the colored hair swatches (Lower the L value, the darker and more intense the hair color).

TABLE 3-2

| Sample | L Value | Ratio of amine number to acid number |
|---|---|---|
| Control | 27.95 | |
| A | 19.76 | 1:1.80 |
| B | 17.81 | 1:1.93 |
| C | 18.35 | 1:1.14 |
| D | 18.22 | 1:0.98 |

4. Study of The Disclosed Composition Used as a Barrier on Hair During the Bleaching or Highlighting Process Objective:

To study the barrier effect of the disclosed composition when applied to hair before bleaching, measured by spectrophotometer.

Procedure:

First take baseline color reading of black Asian hair using a spectrophotometer. Apply treatments as depicted in Table 4-1 (Control is a traditional soap and Test is the disclosed composition with the ratio of the amine number to acid number is 1:0.54). Bleach the treated hair with Matrix® V-lights (using SoLite® 40 vol developer) for 20 minutes at 50° C. Shampoo and dry hair. Measure color. Calculate % ΔE.

TABLE 4-1

| Control | % | Test | % |
|---|---|---|---|
| DI Water | 55.975 | DI Water | 20 |
| MEA | 4.025 | Amodimethicone | 40 |
| Isostearic Acid | 10 | Isostearic Acid | 10 |
| Mineral Oil | 30 | Mineral Oil | 30 |

Results:

Hair pre-treated with the disclosed composition had significantly darker color (% ΔE=5.61) than the hair pre-treated with traditional soap (% ΔE=29.97), i.e., the lower the ΔE value, the darker the color. Therefore the bleach penetrated the traditional soap whereas the disclosed composition protected the hair from the bleach, creating highlighting/lowlighting effects.

Overall the results from experiments 1-4 illustrated the ability of the disclosed composition and method to unexpectedly improve the coloring of hair. Specifically the disclosed composition unexpectedly improves hair color intensity, water-resistance, hair highlighting effect, barrier effect during the bleaching process.

The foregoing description illustrates and describes the present disclosure. Additionally, the disclosure shows and describes only the preferred embodiments of the disclosure, but, as mentioned above, it is to be understood that it is capable of changes or modifications within the scope of the concept as expressed herein, commensurate with the above teachings and/or skill or knowledge of the relevant art. The embodiments described hereinabove are further intended to explain best modes known of practicing the invention and to enable others skilled in the art to utilize the disclosure in such, or other, embodiments and with the various modification required by the particular applications or uses disclosed herein. Accordingly, the description is not intended to limit the invention to the form disclosed herein. Also, it is intended that the appended claims be construed to include alternative embodiments.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

What is claimed:

1. A method for coloring hair comprising applying a composition to hair wherein the composition comprises
   (a) at least one polyamine,
   (b) at least one acid,
   (c) at least one water-insoluble ingredient,
   (d) at least one hair colorant, and
   (e) solvent,
   wherein the molar ratio of the amine groups in the at least one polyamine to the acid groups in the at least one acid is from about 1:0.5 to about 1:30 and wherein a mixture of components (a), (b), (c) and (e) form a mixture that has a receding contact angle of at least about 66 degrees on glass.

2. The method as claimed in claim 1, wherein the composition further comprises at least one auxiliary ingredient (f) wherein the at least one auxiliary ingredient is selected from the group consisting of an amino acid, a protein, a cationic conditioner, a cationic polymer, a anionic surfactant, a nonionic surfactant, an amphoteric surfactant, a zwitterionic surfactant, a viscosity modifier, an organosiloxane polymer, a wax, a silicone resin, a pigment, a powder, a preservative, an antioxidant, a vitamin, an alpha hydroxy acid, a beta hydroxy acid, an alpha ketoacid, an antibacterial agent, a sunscreen, a preservative, a pH adjusting agent, a bleaching agent, a perfume, a sequestering agent, an anti-dandruff agent and mixtures thereof.

3. The method as claimed in claim 1, wherein the at least one polyamine (a) is selected from the group consisting of a polyethyleneimine, a polyvinylamine, an aminated polysaccharide, an amine substituted polyalkylene glycol, an amine substituted polyacarylate crosspolymer, an amine substituted polyacrylate, an amine substituted polymethacrylate, a protein, an amine substituted polyester, a polyamino acid, an amodimethicone, a polyalkylamine, diethylene triamine, triethylenetetramine, spermidine, spermine, amino silicone and mixtures thereof.

4. The method as claimed in claim 1, wherein the at least one polyamine (a) is selected from the group consisting of a polyethyleneimine, a polyvinylamine, chitosan, polylysine, polyacrylate-1 cross-polymer and mixtures thereof.

5. The method as claimed in claim 1, wherein the at least one acid (b) is selected from the group consisting of a fatty carboxylic acid, a fatty ether carboxylic acid, a fatty ether phosphoric acid, a fatty phosphoric acid and mixtures thereof.

6. The method as claimed in claim 1, wherein the at least one acid (b) is a monoacid or a polyacid.

7. The method as claimed in claim 1, wherein the at least one acid (b) is selected from the group consisting of capric acid, caprylic acid, isosteric acid, oleic acid, stearic acid, lauric acid, linoleic acid, linolenic acid, laureth-5 carboxylic acid, laureth-11 carboxylic acid, cetyl phosphosphate, stearyl phosphate, oleth-3 phosphate, oleth-10 phosphate and mixtures thereof.

8. The method as claimed in claim 1, wherein the at least one water-insoluble ingredient (c) is selected from the group consisting of an oil, a fatty ester, a hydrocarbon oil, a silicone, a wax, a fatty acid, a fatty alcohol and mixtures thereof.

9. The method as claimed in claim 1, wherein the at least one water-insoluble ingredient (c) is selected from the group consisting of olive oil, avocado oil, coconut oil, mineral oil, isopropyl palmitate, capric/caprylic triglyceride, isododecane, polyisobutene, dimethicone phenyltrimethicone, beeswax and mixtures thereof.

10. The method as claimed in claim 1, wherein the at least one hair colorant (d) is selected from the group consisting of a bleaching agent, an oxidative dye, a substantive dye, direct dyes, oxidative dyesazoic dyes, sulfur dyes, azomethine dyes, triarylmethane, xanthene dyes, phthalocyanin dyes, phenothiazine dyes, pigments, coloring polymers, direct dyes, oxidation dyes, nacreous pigments, pearling agents, leuco dyes, optical lightening colorants, natural colorants, optically-variable pigments and mixtures thereof.

11. The method as claimed in claim 1, wherein the at least one polyamine (a) is present in a positive amount up to about 30% by weight, based on the weight of the composition.

12. The method as claimed in claim 1, wherein the at least one acid (b) is present in a positive amount up to about 50% by weight, based on the weight of the composition.

13. The method as claimed in claim 1, wherein the at least one water-insoluble ingredient (c) is present in a positive amount up to about 50% by weight, based on the weight of the composition.

14. The method as claimed in claim 1, wherein the at least one hair colorant (d) is present in an amount up from about 0.005 to about 10% by weight, based on the weight of the composition.

15. The method as claimed in claim 1, wherein solvent (e) is present in an amount of from about 10% to about 90% by weight, based on the weight of the composition.

16. The method as claimed in claim 2, wherein the at least one auxiliary ingredient (f) is present in a positive amount up to about 50% by weight, based on the weight of the composition.

17. The method as claimed in claim 1, wherein components (a), (b), (c) and (e) and optionally component (f) are applied to hair and component (d) is subsequently applied to the hair.

18. The method as claimed in claim 1, wherein components (a), (b), (c), (d) and (e) and optionally component (f) are applied to hair simultaneously.

19. The method as claimed in claim 1, wherein component (d) and optionally components (e) and (f) are applied to hair and components (a), (b) (c), (e) and optionally component (f) is subsequently applied to the hair.

20. The method as claimed in claim 1, wherein the coloring agent (d) is applied to hair followed by application of the other components and other portions of the hair have all components except the coloring agent (d) applied followed by application of the coloring agent (d).

21. A method for coloring hair comprising applying a composition to hair wherein the composition comprises
  (a) at least one polyamine selected from the group consisting of a polyethyleneimine, a polyvinyl amine, an aminosilicone, and an amine substituted polyacrylate crosspolymer,
  (b) at least on acid is selected from the group consisting of a fatty carboxylic acid, a fatty ether carboxylic acid, a fatty ether phosphoric acid, and a fatty phosphoric acid,
  (c) at least one water-insoluble ingredient,
  (d) at least one hair colorant, and
  (e) solvent,
  wherein the molar ratio of the amine groups in the at least one polyamine to the acid groups in the at least one acid is from about 1:0.5 to about 1:30 and wherein a mixture of components (a), (b), (c) and (e) form a mixture that has a receding contact angle of at least about 66 degrees on glass.

22. The method as claimed in claim 21, wherein the at least one water-insoluble ingredient (c) is selected from the group consisting of an oil, a fatty ester, a hydrocarbon oil, a silicone, a wax, a fatty acid, a fatty alcohol and mixtures thereof.

23. The method as claimed in claim 21, wherein the at least one water-insoluble ingredient (c) is selected from the group consisting of olive oil, avocado oil, coconut oil, mineral oil, isopropyl palmitate, capric/caprylic triglyceride, isododecane, polyisobutene, dimethicone phenyltrimethicone, beeswax and mixtures thereof.

24. The method as claimed in claim 21 wherein the at least one polyamine is a polyethyleneimine.

25. The method as claimed in claim 21 wherein the at least one polyamine is a polyvinyl amine.

26. The method as claimed in claim 21 wherein the at least one polyamine is an aminosilicone.

27. The method as claimed in claim 21 wherein the at least one polyamine is an amine substituted polyacrylate crosspolymer.

* * * * *